(12) United States Patent
Thalacker et al.

(10) Patent No.: US 11,510,851 B2
(45) Date of Patent: Nov. 29, 2022

(54) APPLICATION DEVICE WITH REDOX INITIATOR SYSTEM, METHOD OF PRODUCTION AND USE THEREOF

(71) Applicant: 3M INNOVATIVE PROPERTIES COMPANY, St. Paul, MN (US)

(72) Inventors: Christoph H. Thalacker, Wilheim (DE); Henry Loll, Gilching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 697 days.

(21) Appl. No.: 16/337,245

(22) PCT Filed: Oct. 2, 2017

(86) PCT No.: PCT/US2017/054764
§ 371 (c)(1),
(2) Date: Mar. 27, 2019

(87) PCT Pub. No.: WO2018/067462
PCT Pub. Date: Apr. 12, 2018

(65) Prior Publication Data
US 2019/0298619 A1 Oct. 3, 2019

(30) Foreign Application Priority Data
Oct. 5, 2016 (EP) ..................................... 16192358

(51) Int. Cl.
*A61K 6/61* (2020.01)
*A61C 3/00* (2006.01)
(Continued)

(52) U.S. Cl.
CPC ................ *A61K 6/61* (2020.01); *A61C 3/005* (2013.01); *A61K 6/30* (2020.01); *A61K 6/64* (2020.01)

(58) Field of Classification Search
CPC ...................................................... A61K 6/61
See application file for complete search history.

(56) References Cited

U.S. PATENT DOCUMENTS

| 4,259,075 A | 3/1981 | Yamauchi |
| 4,368,043 A | 1/1983 | Yamauchi |

(Continued)

FOREIGN PATENT DOCUMENTS

| EP | 0712622 | 5/1996 |
| EP | 1051961 | 11/2000 |

(Continued)

OTHER PUBLICATIONS

Antonucci, "New initiator systems for dental resins based on ascorbic acid", J. Dent. Res., 1979, vol. 58, 1887-1899.

(Continued)

*Primary Examiner* — Michael F Pepitone

(57) ABSTRACT

The invention relates to an application device with a handle part and an application part, the application part having a surface onto which a redox initiator system is located, the redox initiator system comprising either hydrophilic oxidizing agent(s) and hydrophobic reducing agent (s), or hydrophobic oxidizing agent(s) and hydrophilic reducing agent(s). The invention also relates to a kit comprising the application device, a method of producing the application device and a method or curing a curable composition using the application device.

10 Claims, 1 Drawing Sheet

(51) Int. Cl.
*A61K 6/64* (2020.01)
*A61K 6/30* (2020.01)

(56) References Cited

U.S. PATENT DOCUMENTS

| | | | |
|---|---|---|---|
| 4,499,251 | A | 2/1985 | Omura |
| 4,537,940 | A | 8/1985 | Omura |
| 4,539,382 | A | 9/1985 | Omura |
| 4,872,936 | A | 10/1989 | Engelbrecht |
| 5,130,347 | A | 7/1992 | Mitra |
| 5,501,727 | A | 3/1996 | Wang |
| 5,530,038 | A | 6/1996 | Yamamoto |
| 5,688,883 | A | 11/1997 | Klee |
| 6,071,983 | A | 6/2000 | Yamamoto |
| 6,105,761 | A | 8/2000 | Peuker |
| 6,458,868 | B1 | 10/2002 | Okada |
| 6,528,555 | B1 | 3/2003 | Nikutowski |
| 6,939,900 | B2 | 9/2005 | Ario |
| 6,960,079 | B2 | 11/2005 | Brennan |
| 6,982,288 | B2 | 1/2006 | Mitra |
| 6,998,111 | B2 | 2/2006 | Klee |
| 7,097,075 | B2 | 8/2006 | Peuker |
| 7,700,668 | B2 | 4/2010 | Thalacker |
| 2011/0224326 | A1 | 9/2011 | Thalacker |
| 2013/0143176 | A1* | 6/2013 | Thalacker .............. A61C 19/00 433/9 |

FOREIGN PATENT DOCUMENTS

| | | | |
|---|---|---|---|
| EP | 2412361 | 6/2013 | |
| WO | WO 2004-032785 | 4/2004 | |
| WO | WO 2004-060327 | 4/2004 | |
| WO | WO 2007-121160 | 10/2007 | |
| WO | WO 2012-015814 | 2/2012 | |
| WO | WO 2015-181277 | 12/2015 | |
| WO | WO 2016-007453 | 1/2016 | |
| WO | WO-2016007453 A1 * | 1/2016 | .............. A61K 6/77 |

OTHER PUBLICATIONS

Viswanadhan, "Atomic Physicochemical Parameters for Three Dimensional Structure Directed Quantitative Structure-Activity Relationships", J. Chem. Inf. Comput. Sci., 1989, vol. 29, 163-172.

International search report for PCT International Application No. PCT/US2017/054764 dated Dec. 15, 2017, 4 pages.

* cited by examiner

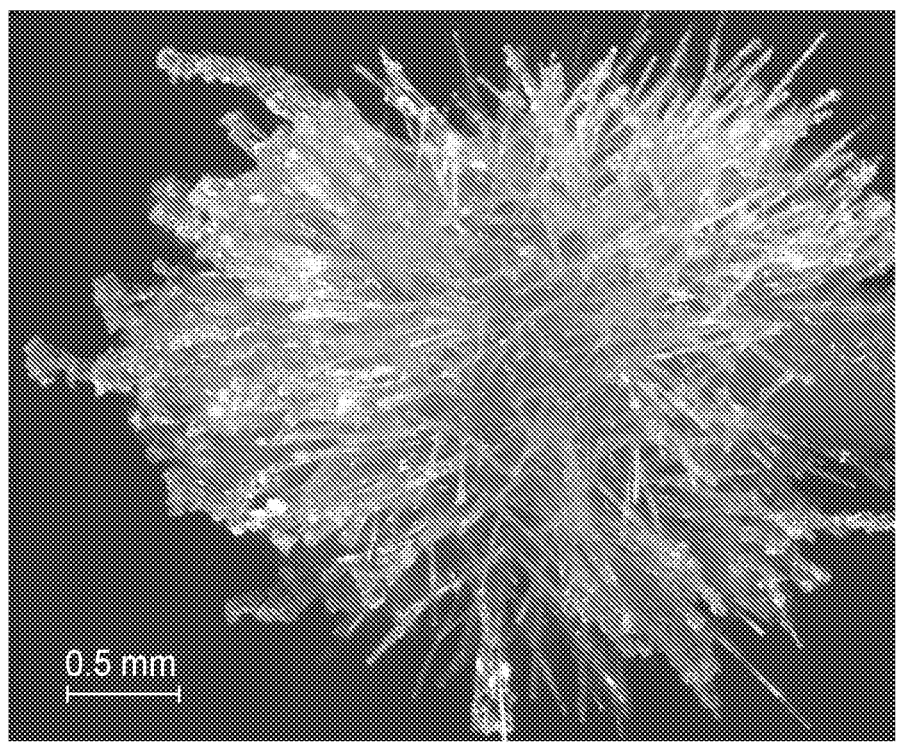

ID# APPLICATION DEVICE WITH REDOX INITIATOR SYSTEM, METHOD OF PRODUCTION AND USE THEREOF

CROSS REFERENCE TO RELATED APPLICATIONS

This application is a national stage filing under 35 U.S.C. 371 of PCT/US2017/054764, filed Oct. 2, 2017, which claims the benefit of European Application No. 16192358.6, filed Oct. 5, 2016, the disclosure of which is incorporated by reference in its/their entirety herein.

FIELD OF THE INVENTION

The invention relates to an application device with a redox initiator system contained on its surface.

The redox initiator system is suitable for hardening curable compositions in particular in the dental and orthodontic field.

BACKGROUND ART

While many modern dental restorative materials are based on photo initiated radical polymerization of (meth)acrylates, there is an increased interest in materials that also have a dark cure or redox initiator system, making them dual cure.

For storage stability reasons, the components of the redox partners need to be split between two formulations (e.g. pastes, liquids or powders) which are mixed immediately before use in order to initiate the dark cure reaction.

Traditionally, most of these redox systems consist of a peroxide as an oxidizing agent and an aromatic amine as an electron donor.

However, sometimes redox initiator systems based on the combination of peroxide and amines may cause difficulties, e.g. due to
  discoloration through oxidation of the amine;
  limited shelf life, especially for peroxide containing formulations;
  low degree of conversion and therefore less strength of the material compared to light cure; and/or
  incompatibility with acidic formulations, such as self-adhesive resin cements and bonding agents.

Thus, there is a need for an alternative redox initiator system.

In WO 2016/007453 A1 (Hecht et al.) an initiator system comprising an ascorbic acid component, a transition metal component and an organic peroxide is described. The initiator system can be contained in a kit of parts for dental use, wherein the ascorbic acid component and the organic peroxide component are contained in different parts of the kit of part.

WO 2012/015814 (Thalacker et al.) describes a kit of parts comprising part A and part B, wherein part A comprises polymerizable components with an acid group and an initiator or an initiator system and part B comprises activator(s) and a film or film former(s) with a molecular weight at least about 1,000. The film may be located on the surface of an applicator or packaging material or well of a packaging device.

J. M. Antonucci, C. L. Grams, D. J. Termini: "New initiator systems for dental resins based on ascorbic acid", J. Dent. Res. 1979, 58, 1887-1899 describe the use of an initiator system involving a peroxide, an ascorbic acid derivative, and a copper salt.

U.S. Pat. No. 5,501,727 (Wang et al.) discloses a curable dental composition comprising an ethylenically unsaturated moiety, an oxidizing agent and metal complexed ascorbic acid.

U.S. Pat. No. 5,688,883 (Klee et al.) discloses a polymerizable composition formed by mixing a liquid and a powder composition, where the liquid includes a peroxide, and the powder comprises a proton donor (e.g. an ascorbic acid derivative) and a metal containing compound.

U.S. Pat. No. 6,998,111 (Klee et al.) discloses storage stable polymerizable compositions including a peroxide, a metal containing material, and a protected reducing agent (e.g. ascorbic acid bearing protecting groups).

U.S. Pat. No. 6,071,983 (Yamamoto et al.) discloses a primer composition and curable composition which may be prepared and applied using a tool carrying at least part of the polymerization initiator.

WO 2015/181277 (Weiss) describes a micro applicator with metal containing additives coated thereon for use with dental adhesives.

U.S. Pat. No. 4,368,043 (Yamauchi et al.) describes an adhesive cementing agent containing a phosphoric or phosphonic acid ester compound with at least one polymerizable functional group. The adhesive cementing agent further comprises a curing agent, e.g. a combination of a peroxide, amine and sulfinate.

SUMMARY OF INVENTION

In view of the above, it is an object of the invention to provide a redox initiator system which addresses at least one or more of the issues reported above.

In particular, it would be desirable to have a redox initiator system which can be used in acidic environment for hardening radically curable components.

In addition or alternatively, it would be desirable, if the redox initiator system is sufficiently storage stable and easy to use. If possible, the need for conducting separate mixing steps should be avoided.

Further, it would be desirable, if the redox initiator system leads to sufficient or even improved physical properties of the cured composition like adhesion. The invention described in the present text addresses one or more of these objects.

In one embodiment the invention features an application device with a handle part and an application part, the application part having a surface onto which a redox initiator system is located, the redox initiator system comprising either hydrophilic oxidizing agent(s) and hydrophobic reducing agent (s), or hydrophobic oxidizing agent(s) and hydrophilic reducing agent(s).

According to another embodiment, the invention relates to an application device with a handle part and an application part, the application part having a surface onto which a redox initiator system is located, the redox initiator system comprising: either
  hydrophilic oxidizing agent(s), a hydrophilic transition metal component and
  hydrophobic reducing agent (s), or
  hydrophobic oxidizing agent(s), a hydrophilic transition metal component and hydrophilic reducing agent(s).

According to a further embodiment, the invention relates to an application device with a handle part and an application part, the application part having a surface onto which a redox initiator system is located, the redox initiator system comprising: either an ascorbic acid component having a log P or log D value A1, a peroxide component having a log P or log D value B1, and optionally a transition metal component having a log P or log D value C1, or an ascorbic acid component having a log P or log D value A2, a peroxide component having a log P or log D value B2, and optionally a transition metal component having a log P or log D value C2, wherein the difference between A1 and B1≥2 or 3 or
the difference between A2 and B2≥2 or 3 wherein P is the octanol-water partition coefficient for neutral components and D is the octanol-water distribution coefficient for components having ionisable groups, each calculated for a pH of 2.7, and wherein the respective components are as described in the present text.

In another embodiment, the invention relates to a method of using the application device as described in the present text for initiating a curing reaction of curable components as described in the present text.

A further embodiment of the invention is directed to a kit of parts comprising the application device as described in the present text and a composition comprising curable components as described in the present text.

The invention is also related to a method of curing a composition comprising curable components as described in the present text, the method comprising the step of bringing the application part of the application device as described in the present text in contact with the curable components.

Yet a further aspect of the invention is directed to a method for producing an application device as described in the present text, the method comprising the steps of a. applying a hydrophobic reducing agent (e.g. ascorbic acid component) as described in the present text together with a solvent to the surface of the application part of the application device, b. evaporating the solvent, c. applying a hydrophilic oxidizing agent (e.g. peroxide component) and optionally a hydrophilic transition metal component (e.g. copper component) as described in the present text together with a solvent to the surface of the application part of the application device, d. evaporating the solvent, e. optionally applying a film forming component after step (a) or step (d) or after step (a) and (d), or together with the hydrophilic components of step (c), f. optionally conducting a drying step.

wherein the steps are applied in the order (a), (b), (c), (d) or (c), (d), (a), (b), or i. applying a hydrophilic reducing agent (e.g. ascorbic acid component) as described in the present text together with a solvent to the surface of the application part of the application device, ii. evaporating the solvent, iii. applying a hydrophobic oxidizing agent (e.g. peroxide component) and optionally a hydrophilic transition metal component (e.g. copper component) as described in the present text together with a solvent to the surface of the application part of the application device, iv. evaporating the solvent, v. optionally applying a film forming component after step (ii) or step (iv) or after step (ii) and (iv) or together with the hydrophilic components of step (i), vi. optionally conducting a drying step, wherein the steps are applied in the order (i), (ii), (iii), (iv) or (iii), (iv), (i), (ii).

BRIEF DESCRIPTION OF FIGURES

FIG. 1 shows a sample of a suitable application device having the shape of a microbrush, impregnated with a redox initiator system according to the present invention.

Within the description of the present text, the following terms are defined as follows:

A "dental composition" is any composition which can be used in the dental field or orthodontic area. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from 15 to 50° C. or from 20 to 40° C. within a time frame of about 30 min or about 20 min or about 10 min.

Higher temperatures are not recommended as they might cause pain to the patient and may be detrimental to the patient's health.

Dental compositions are typically provided to the practitioner in comparable small volumes, that is volumes in the range from 0.05 to 100 ml or from 0.1 to 50 ml or from 0.2 to 10 ml or from 0.5 to 2 ml.

The term "compound" or "component" is a chemical substance which has a particular molecular identity or is made of a mixture of such substances, e.g., polymeric substances.

By "paste" is meant a soft, viscous mass of solids (i.e. particles) dispersed in a liquid.

A "hardenable compound or material" is any compound which can be cured or solidified e.g. by heating to cause polymerization, chemical crosslinking, radiation-induced polymerization or crosslinking or using a redox initiator. A hardenable compound may contain only one, two, three or more polymerizable groups. Typical examples of polymerizable groups include epoxy groups and unsaturated carbon groups, such as a vinyl group being present inter alia in a (methyl)acrylate group.

A "film forming component" is a substance which will cause a composition containing it to change from a liquid stage to a solid stage in such a manner as to form a film or coating on a surface. A definition of the term "film former" can also be found in DIN 55945 (1999-07-00). A film former is typically part of a binder system. The term "film former" is often used in varnishes. The substance hydroxyethyl methacrylate (HEMA) cannot be regarded as a film former according to this definition.

A "film" is a thin sheet or strip of a preferably flexible material. A coating of a surface with a material typically results in a film.

An "ethylenically unsaturated acidic compound" is meant to include monomers, oligomers, and polymers having ethylenic unsaturation and acid and/or acid-precursor functionality. Acidic-precursor functionalities include, e.g. anhy drides, acid halides and pyrophosphates. The acidic group preferably comprises one or more carboxylic acid residues, such as —COOH or —CO—O—CO—, phosphoric acid residues, such as —O—P(O)(OH)OH, or sulfonic acid residues, such as —SO$_3$H.

An "initiator" is a substance being able to catalytically initiate a chemical reaction, preferably via a free radical reaction. The initiator can be a single compound or can comprise more than one component, such as a combination of a sensitizing agent with a reducing agent. Depending on the reaction conditions chosen (e.g. pH-value >7 or pH-value <7) different initiators can be preferred.

A "redox initiator system" is defined as the combination of reducing agent(s) and oxidizing agent(s) being located on the application part of the application device. If present, transition metal component(s) are also regarded as components of the redox initiator system.

A mixture or solution is considered to be "homogeneous", if it appears clear to the human eye, and essentially no settling of the filler or separation of components can be visually detected within a given time period (e.g. 24 hours after preparation of the composition). In addition, this can be proven by analysing the particle size distribution of the composition. A dispersion or mixture is considered to be "homogeneous", if the particle size of the particles in 50% of the analysed volume is in a range below about 1 μm, wherein the particle size distribution is measured as described in the text below.

A "dispersion" is a homogeneous mixture of different components, especially the distribution of solid particles in a liquid. If only liquid components are concerned and no solid particles are present, the mixture can also be classified as emulsion. If the size of the solid particles is very low, such that the presence of individual particles cannot be identified by the human eye, a dispersion sometimes looks like a clear or slightly cloudy solution.

As used herein "adhesive" or "dental adhesive" refers to a composition used as a pre-treatment on a dental structure (e.g., a tooth) to adhere a "dental material" (e.g., a "restorative", an orthodontic appliance (e.g., bracket), or an "orthodontic adhesive") to the dental structure. An "orthodontic adhesive" refers to a composition used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, "hardening" or "curing" a composition are used interchangeably and refer to polymerization and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental surface" refers to tooth structures (e.g., enamel, dentin, and cementum) and bone.

As used herein, "(meth) acryl" is a shorthand term referring to "acryl" and/or "methacryl". For example, a "(meth) acryloxy" group is a shorthand term referring to either an acryloxy group (i.e., CH$_2$=CH—C(O)—O—) and/or a methacryloxy group (i.e., CH$_2$=C(CH$_3$)—C(O)—O—).

An "ascorbic acid component" is a component comprising the following structural element:

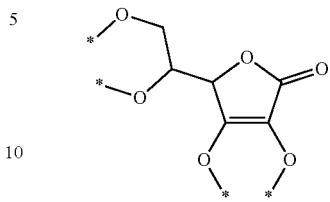

wherein the symbol "*" indicates a connection to another chemical moiety or atom.

A common measure for the hydrophilic ("water loving") or hydrophobic ("water fearing") character of a chemical compound is the partition coefficient P (or distribution coefficient D for ionizable compounds). It is the ratio of concentrations of a compound in a mixture of two immiscible phases at equilibrium, most often n-octanol and water. High partitioning coefficient values are conveniently given in the form of their logarithm to the base 10, i.e. log P or log D.

Typically, the log P value is given as follows:

$$\log P_{octanol/water} = \log([solute]_{octanol}[solute])water,$$

The higher the log P value, the more hydrophobic the nature of the solute is.

For components having ionisable groups, the octanol-water partition coefficient is given by the respective D value (distribution coefficient), typically at a given pH value.

In the present text the log P or log D values were calculated using the computer software provided on www.chemicalize.org (ChemAxon Kft, Budapest, Hungary).

This software allows for a computerized calculation of log P or log D values based on the respective chemical formula and a pool of predefined fragments. This method is described in more detail in V. N. Viswanadhan, A. K. Ghose, G. R. Revankar, R. K. Robins, "Atomic Physicochemical Parameters for Three Dimensional Structure Directed Quantitative Structure-Activity Relationships", J. Chem. Inf. Comput. Sci. 1989, Vol. 29, 163-172. According to this method every fragment is assigned a unique name and value. Thus, the log P value of a molecule is the sum of the fragment values that are present in the molecule.

Compounds or agents with a calculated log P (or log D) value >=2 or 3 are typically considered "hydrophobic" in the sense of the present text.

Compounds or agents with a calculated log P (or log D) value <=1 are typically considered "hydrophilic" in the sense of the present text.

The combinations of hydrophilic oxidizing agents and hydrophobic reducing agents or hydrophobic oxidizing agents and hydrophilic reducing agents according to the present text are characterized in that their log P or log D values differ by about 2, 3 or more.

Thus, the so-called hydrophilic compounds (e.g. oxidizing or reducing agent) can also have a log P or log D value higher than 1 if the log P or log D value of the so-called hydrophobic compound (e.g. reducing or oxidizing agent) is high enough so that the difference is greater or equal to about 2 or 3.

In the present text the log P or log D were calculated for a pH value of 2.7. This is the pH value commercially available dental adhesives typically have.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A composition can be classified as "storage stable", if it remains stable over a considerable long period of time (at least about 4 weeks to more than about 12 months under ambient conditions). A storage stable composition does typically not show decomposition of the components contained therein or premature polymerization over time. Moreover, physical and material properties of the composition (such as curing behaviour, mechanical properties and adhesion performance shall not diminish more than desired during storage.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and a relative humidity of about 50%. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of properties such as contrast ratio and so forth used in the specification and claims are to be understood as number as such and also as being modified in all instances by the term "about." Any numerical value, inherently contains certain errors necessarily resulting from the standard deviations found in their respective testing measurements.

The term "about" can allow for a degree of variability in a value or range, e.g. within 10% or within 5% or within 1% of a given value or a given limit of a range.

"And/or" means one or both. E.g., the expression component A and/or component B refers to a component A alone, component B alone, or to both component A and component B.

DETAILED DESCRIPTION

The invention described in the present text provides a couple of advantages.

This application device containing the redox initiators system described in the present text is in particular suitable for curing radically polymerizable components e.g. (meth) acrylate based compositions, including self-etching (i.e. acidic) dental adhesives.

When the curable composition is picked up and applied with the application device described in the present text, the initiator components located on the surface of the application device are dissolved in the composition and initiate the curing reaction, thus eliminating the need for a separate mixing step to be performed.

In contrast to existing systems where at least one part of the redox initiator system (e.g. a peroxide) is provided in the composition, potential shelf life issues with respect to this component are avoided.

As the redox initiator system is provided during storage separately from curable components and is combined with curable components shortly before use, the redox initiator system is basically compatible with all kinds of curable components. Also, dark curing of already available light curable compositions is now possible.

It was found, that applying the commercially available dental adhesive Scotchbond™ Universal (3M Oral Care; 3M ESPE) with an application device as described in the present text to an enamel or dentin surface of a tooth results in high bond strength even without conducting a light curing step.

Similarly, using the application device described in the present text in combination with the commercially available adhesive Scotchbond™ Universal (3M Oral Care; 3M ESPE) and the commercially available resin cement RelyX™ Ultimate (3M Oral Care; 3M ESPE) in dark cure mode provides the same high level of bond strength to dentin or enamel as in light cure mode.

Thus, the invention described in the present text addresses one or more of the following issues:
reduced shelf life of compositions containing ethylenically unsaturated acidic components with oxidizing agents like peroxide, peroxide and copper, reducing agents like ascorbic acid or ascorbic acid components,
reduced compatibility of ascorbic acid components with copper salts;
reduced compatibility of peroxide components with ascorbic acid components in solutions or pastes.

The application device described in the present text comprises a redox initiator system.

The redox initiator system described in the present text is in particular suitable for curing radically curable components under ambient conditions (e.g. 20 to 40° C.) within a reasonable time period (e.g. 1 to 10 min).

The redox initiator system located on the surface of the application device is provided in dry form. The components of the redox initiator system are not provided as a liquid composition.

The redox initiator system described in the present text comprises the following components:
hydrophilic or hydrophobic reducing agent;
hydrophilic or hydrophobic oxidizing agent.

According to one embodiment the redox initiator system comprises the following components:
reducing agent being an ascorbic acid component,
oxidizing agent being a peroxide component, and
accelerator component being a transition metal component.

The respective components can be provided either as hydrophilic or hydrophobic components.

If desired, the components of the redox initiator system can be characterized by their respective log P or log D values.

According to one embodiment, the log P or log D values of the hydrophilic oxidizing agent and hydrophobic reducing agent or log P or log D values of the hydrophobic oxidizing agent and hydrophilic reducing agent differ from each other by a number of at least 2 or 3.

Ionisable groups include the following moieties: —COOH, —SO$_3$H, —O—P(O)$_2$OH, —NH$_2$, —NHR, —NR$_2$.

The respective values for P or D are given in logarithmic form. Log D or P values are given for pH 2.7, which is a pH value commercially available adhesives such as Scotchbond™ Universal, manufactured by 3M Oral Care, typically have.

The nature of the hydrophilic oxidizing agent is not particularly limited. The hydrophilic oxidizing agent should be suitable to address at least one or more of the objects outlined above.

Hydrophilic oxidizing agents known in the art and used in the dental field include persulfate(s), percarbonate(s) and peroxide(s).

The hydrophilic oxidizing agent is typically used in the following amounts:
  lower amount: at least 10 or at least 20 or at least 30 wt. %;
  higher amount: utmost 70 or utmost 80 or utmost 90 wt. %;
  range: from 10 to 90 wt. % or from 20 to 80 wt. % or from 30 to 70 wt. %; wt. % with respect to weight of the redox initiator system.

According to one embodiment the redox initiator system described in the present text comprises a hydrophilic peroxide as oxidizing agent.

In particular, peroxides being solid at room temperature were found to be useful.

Hydrophilic oxidizing agents typically have a log P or Log D value of <=1 (at pH 2.7).

Examples of hydrophilic oxidizing agents include persulfates, peroxides and percarbonates like sodium persulfate (log D: −5.56), potassium persulfate (log D: −5.69), ammonium persulfate (log D: −5.69), sodium perborate (log D: −6.06), potassium perborate, ammonium perborate, sodium percarbonate (log D: 0.17), potassium percarbonate (log D: 0.79), urea peroxide (log P: −1.36).

Other examples of the hydrophilic peroxide include organic hydroperoxides, in particular hydroperoxides comprising the structural moiety

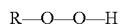

with R being (e.g. C$_1$ to C$_6$ or C$_3$ to C$_6$) alkyl, or branched alkyl, (e.g. C$_3$ to C$_6$).

An example of a suitable hydroperoxides is t-butyl hydroperoxide (log P: 0.98).

According to one embodiment, the hydrophilic peroxide is used in excess with respect to the weight of the component comprising the ascorbic acid moiety.

The nature of the hydrophobic reducing agent is not particularly limited. The hydrophobic reducing agent should be suitable to address at least one or more of the objects outlined above.

In particular, reducing agents being solid at room temperature were found to be useful.

Hydrophobic reducing agents typically have a log P/D value of >=1.5 or 2 or 3 (at pH 2.7).

Hydrophobic reducing agents include, for example, amines like ethyl 4-dimethylaminobenzoate (log D: 2.03), methyl 4-dimethylaminobenzoate (log D: 1.67), N,N-dimethyl-p-toluidine (log D: 2.59), and iso-amyl 4-dimethylaminobenzoate (log D: 3.28), ascorbic acid components functionalized with long alkyl chains (e.g. C$_5$ to C$_{30}$) like the ones cited below.

For some components the respective log P or log D value is given in brackets (for pH 2.7).

The hydrophobic reducing agent is typically used in the following amounts:
  lower amount: at least 5 or at least 10 or at least 20 wt. %;
  higher amount: utmost 45 or utmost 40 or utmost 30 wt. %;
  range: from 5 to 45 wt. % or from 10 to 40 wt. % or from 20 to 30 wt. %;
  wt. % with respect to weight of the redox initiator system.

According to one embodiment the redox initiator system described in the present text comprises a hydrophobic ascorbic acid as reducing agent.

Examples of the hydrophobic ascorbic acid component include esters of ascorbic acid which are formed by reacting one or more of the hydroxyl functions of ascorbic acid with a carboxylic acid, in particular the C$_5$ to C$_{30}$ carboxylic acid.

Suitable examples of C$_5$ to C$_{30}$ carboxylic acids include the fatty acids, like caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

Using an ascorbic acid moiety containing component having in addition a hydrophobic moiety can be preferred. Suitable hydrophobic moieties include saturated and unsaturated aliphatic residues (e.g. C$_5$ to C$_{30}$ or C$_{12}$ to C$_{30}$). Those ascorbic acid derivatives may also function as surface-active substances (substances having a so-called "head/tail structure").

Particularly preferred are ascorbyl decanoate (log D: 2.33), ascorbyl laurate (log D: 3.22), ascorbyl myristate (log D: 4.12), ascorbyl palmitate (log D: 5.01), ascorbyl stearate (log D: 6.51), ascorbyl oleate (log D: 6.15) mixtures and salts thereof.

For some components the respective log P or log D value is given in brackets (for pH 2.7).

The nature of the hydrophobic oxidizing agent is not particularly limited. The hydrophobic oxidizing agent should be suitable to address at least one or more of the objects outlined above.

The hydrophobic oxidizing agent is typically used in the following amounts:
  lower amount: at least 10 or at least 20 or at least 30 wt. %;
  higher amount: utmost 70 or utmost 80 or utmost 90 wt. %;
  range: from 10 to 90 wt. % or from 20 to 80 wt. % or from 30 to 70 wt. %;
  wt. % with respect to weight of the redox initiator system.

According to one embodiment the redox initiator system described in the present text comprises a hydrophobic peroxide as oxidizing agent.

Examples of the hydrophobic peroxide include organic peroxides and mixtures thereof.

Hydrophobic oxidizing agents typically have a log P value of >=2 or 3 (at pH 2.7).

According to one embodiment, the organic peroxide is a di-peroxide, preferably a di-peroxide comprising the moiety R$_1$—O—O—R$_2$—O—O—R$_3$, with R$_1$ and R$_3$ being independently selected from H, alkyl (e.g. C$_1$ to C$_6$), branched alkyl (e.g. C$_1$ to C$_6$), cycloalkyl (e.g. C$_5$ to C$_{10}$), alkylaryl (e.g. $C_7$ to $C_{12}$) or aryl (e.g. $C_6$ to $C_{10}$) and $R_2$ being selected from alkyl (e.g. $C_1$ to $C_6$) or branched alkyl (e.g. $C_1$ to $C_6$).

Examples of organic di-peroxides include 2,2-Di-(tert.-butylperoxy)-butane and 2,5-Dimethyl-2,5-di-(tert-butylperoxy)-hexane and mixtures thereof.

Other peroxides are ketone peroxide(s), diacyl peroxide(s), dialkyl peroxide(s), peroxyketal(s), peroxyester(s) and peroxydicarbonate(s).

Examples of ketone peroxides include methyl ethyl ketone peroxide, methyl isobutyl ketone peroxide, methyl cyclohexanone peroxide, and cyclohexanone peroxide.

Examples of peroxyesters include alpha-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate and t-butylperoxymaleic acid.

Examples of peroxidicarbonates include di-3-methoxybutyl peroxidicarbonate, di-2-ethylhexyl peroxydicarbonate, bis(4-t-butylcyclohexyl)peroxidicarbonate, diisopropyl-1-peroxydicarbonate, di-n-propyl peroxidicarbonate, di-2-ethoxyethyl-peroxidicarbonate, and di allyl peroxidicarbonate.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxides include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Examples of peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butylester.

Examples of hydroperoxides include p-diisopropylbenzene hydroperoxide, cumene hydroperoxide, pinane hydroperoxide, p-methane hydroperoxide and 1,1,3,3-tetramethylbutyl hydroperoxide and mixtures thereof.

Particularly useful oxidizing agents include dibenzoyl peroxide (log P: 3.95), tert.Butylperoxy-3,5,5-trimethylhexanoate (TBPIN) (log P: 4.04), dilauryl peroxide (log P: 9.24), tetramethylbutyl hydroperoxide (TMBHP) (log P: 2.54), 2,2-di-(tert-butylperoxy)butane (log P: 3.78) and 2,5-dimethyl-2,5-di-(tert-butylperoxy)hexane (log P: 4.53).

The nature of the hydrophilic reducing agent is not particularly limited. The hydrophilic reducing agent should be suitable to address at least one or more of the objects outlined above.

Hydrophilic reducing agents typically have a log P/D value of $<=1$ (at pH 2.7)

Hydrophilic reducing agents known in the art and used in the dental field include sulfinate salts, thiourea derivatives, triethanolamine, ascorbic acid and mixtures thereof.

Examples of sulfinate salts are sodium benzene sulfinate (log D: −0.39), potassium benzene sulfinate, ammonium benzene sulfinate, sodium toluene sulfinate (log D: 0.29), potassium toluene sulfinate, ammonium toluene sulfinate.

For some components the respective log P or log D value is given in brackets (for pH 2.7).

The hydrophilic reducing agent is typically used in the following amounts:
 lower amount: at least 5 or at least 10 or at least 20 wt. %;
 higher amount: utmost 45 or utmost 40 or utmost 30 wt. %;
 range: from 5 to 45 wt. % or from 10 to 40 wt. % or from 20 to 30 wt. %;
 with respect to weight of the redox initiator system.

According to one embodiment the redox initiator system described in the present text comprises a hydrophilic ascorbic acid as reducing agent.

Examples of the hydrophilic ascorbic acid component comprise ascorbic acid (log D: −1.92), sodium ascorbate (log D: −1.98), potassium ascorbate, ammonium ascorbate, calcium ascorbate and mixtures thereof.

According to one embodiment, the application device described in the present text comprises a hydrophilic or hydrophobic transition metal component.

Hydrophilic transition metal components typically have a log P value of $<=1$ (for pH 2.7).

Hydrophobic transition metal components typically have a log P value of $>=2$ or 3 (for pH 2.7).

Suitable transition metal component(s) include organic and/or inorganic salt(s) from titanium, vanadium, chromium, manganese, iron, cobalt, nickel, copper and/or zinc, with copper and iron being sometimes preferred.

Useful salts include acetate(s), chloride(s), sulphate(s), benzoate(s), acetylacetonate(s), naphthenate(s), carboxylate(s), bis(1-phenylpentan-1,3-dione) complexes, salicylate(s), complexes with ethylenediaminetetraacetic acid of either of the transition metals and mixtures thereof.

According to one embodiment, the transition metal component is in an oxidation stage, which allows the component to be reduced. Useful oxidation stages include +2, +3, +4, +5, +6 and +7, as applicable.

For some components the respective log P or log D value is given in brackets (for pH 2.7).

According to one embodiment, the transition metal component comprises a copper component.

The copper component may be a hydrophobic copper component or a hydrophilic copper component.

If the copper component is a hydrophilic copper component it is typically used in combination with a hydrophobic ascorbic acid component and a hydrophilic peroxide component.

If the copper component is a hydrophobic copper component it is typically used in combination with a hydrophilic ascorbic acid component and a hydrophobic peroxide component.

The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper salicylate, complexes of copper with thiourea, ethylenediaminetetraacetic acid and/or mixtures thereof. The copper compounds can be used in hydrated form or free of water. Especially preferred is copper acetate.

Examples of the hydrophobic copper component include copper 2-ethylhexanoate (log D: 2.80), copper naphthenate, copper bis(1-phenylpentan-1,3-dione) complex (copper procetonate) (log D: 2.45), copper salicylate (log D: 1.72) and mixtures thereof.

Examples of the hydrophilic copper component include copper (II) chloride (log P: 0.61); copper (II) acetate monohydrate (log D: −0.23) and mixtures thereof.

If present, the transition metal component (e.g. copper component) is typically used in the following amounts:
  lower amount: at least 0.01 or at least 0.1 or at least 1 wt. %;
  higher amount: utmost 20 or utmost 15 or utmost 10 wt. %;
  range: from 0.01 to 20 wt. % or from 0.1 to 15 wt. % or from 1 to 10 wt. %;
with respect to weight of the redox initiator system.

According to one embodiment, the components of the redox initiator system are contained in or covered by or applied with film forming component(s) or composition containing film forming component(s).

These film forming components are suitable to improve adherence of the components of the redox initiator system to the surface of the application device.

If film forming component(s) are present, the components of the redox initiator system are typically dissolved or dispersed in the film forming component(s) and form together with the film forming component(s) a film on the surface of the application device.

The molecular weight (Mw) of the film forming component can vary over a wide range (e.g. from at least about 1,000 to about 1,200,000). Typical ranges include from about 10,000 to about 400,000, or from about 20,000 to about 200,000.

If desired, the molecular weight can be determined by GPC technology, using e.g. a polystyrene standard.

If the molecular weight of the film forming component is too low, the film forming component might not be able to form a sufficiently durable film or coating. Thus, the effect of a delayed release of the activator might not be obtained. E.g., components like 2-hydroxyethyl acrylate (HEMA), which are sometimes classified as film-forming agents, are not suitable as film forming component in the sense of the invention.

The film caused or produced by the film forming component typically has a thickness in a range from 0.5 μm to 100 μm or from 10 μm to 50 μm.

Film formers or film forming components can be classified as natural film former, semi-synthetic film formers, cellulose derivatives, poly(meth)acrylates and vinyl polymers.

Examples of natural film forming components include shellac, mastix, sandarac, tolubalsam, dammar resin, benzoe resin, keratin, maizin, gum Arabic and gelatines.

Examples of semi-synthetic film forming components include gelatines treated with formaldehyde and salol (acetaldehyde phenol condensate).

Typical cellulose derivatives include cellulose acetate phthalate, hydroxyethylcellulose, hydroxypropylcellulose, methylcellulose, ethylcellulose and hydroxypropylmethyl cellulose phthalate.

Examples of poly(meth)acrylates include copolymers of (meth)acrylic esters and amino functional (meth)acrylates, copolymers of (meth)acrylic acid and methyl methacrylate, polyacrylamide, polyacrylic acid and salts thereof, in particular partial salts thereof, including sodium salts.

Examples of vinyl polymers include polyvinyl pyrrolidon, polyvinyl acetate phthalate (e.g. hydroxypropyl- and hydroxypropyl-methylcellulose), homo- and copolymers of polyvinylacetate, homo- and copolymers of polyvinylpropionate, styrene acrylics, ethylene vinyl acetate, poly(hydroxyethyl methacrylate), poly(vinylethylene glycol acrylate, polyvinyl alcohol(s).

Particular examples for film forming component(s) include (e.g. fully or partially hydrolyzed) polyvinylalcohol, polymethylvinylether, polyvinylpyrrolidone, (e.g. aqueous) acrylic resin dispersions (e.g. Eudragit™, commercially available from Röhm), gelatine, polysaccharides (e.g. agarose), polyacrylamide, copolymers of vinylpyrrolidinone and acrylamide, hydrophilic cellulose derivatives (e.g. hydroxyethylcellulose, hydroxypropylcellulose, methylcellulose), homo- and copolymers of polyvinylacetate, homo- and copolymers of polyvinylpropionate, styrene acrylics, ethylene vinyl acetate, polyurethanes, hydroxylated acrylates such as poly(hydroxyethyl methacrylate), poly(vinylethylene glycol acrylate), and combinations and mixtures thereof.

Suitable film forming components are also described in EP 2 412 361 A1 (Thalacker et al.). The content of this reference is herewith incorporated by reference.

Examples of film forming components which are sometimes preferred include polyvinyl alcohol, gelatine, polyacrylic acid, partially neutralized polyacrylic acid and mixtures thereof.

If present, the film forming component(s) are present in the following amounts:
  lower amount: at least 5 or at least 10 or at least 20 wt. %;
  higher amount: utmost 90 or utmost 80 or utmost 70 wt. %;
  range: from 5 to 90 wt. % or from 10 to 80 wt. % or from 20 to 70 wt. %;
with respect to weight of the whole composition being present on the application part of the application device According to one embodiment, the component(s) of the redox initiator system are present in excess compared to the film forming component(s).

The respective components of the composition being present on the application part of the application device are typically present in the following amounts:
  (hydrophilic or hydrophobic) reducing agent: from 5 to 50 or from 10 to 40 wt. %;
  (hydrophilic or hydrophobic) oxidizing agent: from 30 to 80 or from 50 to 70 wt. %;
  film forming component: from 0 to 50 or from 10 to 40 wt. %;
with respect to the weight of the whole composition.

These amounts were found to be particular useful in particular if the redox initiator system is used for curing compositions containing radically curable components in combination with acidic components.

According to one embodiment the respective components are typically present in the following amounts:
  (hydrophilic or hydrophobic) ascorbic acid component: from 5 to 50 or from 10 to 40 wt. %;
  (hydrophilic or hydrophobic) peroxide component: from 30 to 80 or from 50 to 70 wt. %;
  (hydrophilic or hydrophobic) transition metal component: from 0.01 to 20 or from 1 to 15 wt. %;
  film forming component: from 0 to 50 or from 10 to 40 wt. %;
wt. % with respect to the weight of the whole composition.

According to one embodiment, the components of the redox initiator system described in the represent text are not provided in micro encapsulated form.

Embodiments of preferred application device include:

Embodiment 1

An application device with a handle part and an application part, the application part having a surface onto which a redox initiator system is located, the redox initiator system comprising either
- a hydrophobic ascorbic acid component in an amount from 5 to 50 wt. %,
- a hydrophilic peroxide component in an amount from 30 to 80 wt. %, and
- a hydrophilic transition metal component like a copper or iron component in an amount from 0.1 to 15 wt. %, or
- a hydrophilic ascorbic acid component in an amount from 5 to 50 wt. %,
- a hydrophobic peroxide component in an amount from 30 to 80 wt. %, and
- a hydrophobic transition metal component like a copper or iron component in an amount from 0.1 to 15 wt. %, wt. % with respect to the amount of the redox initiator system including the transition metal component,
wherein the redox initiator system including the transition metal component is optionally dissolved or dispersed in or coated with a film forming component and wherein the components are as described in the present text.

Embodiment 2

An application device with a handle part and an application part, the application part having a surface onto which a redox initiator system is located, the redox initiator system comprising either
- an ascorbic acid component selected from ascorbyl octanoate, ascorbyl decanoate, ascorbyl laurate, ascorbyl myristate, ascorbyl palmitate, ascorbyl stearate, ascorbyl oleate mixtures and salts thereof in an amount from 5 to 50 wt. %,
- an oxidizing agent selected from sodium persulfate, potassium persulfate, ammonium persulfate, sodium perborate, potassium perborate, ammonium perborate, sodium percarbonate, potassium percarbonate, urea peroxide or mixtures thereof in an amount from 30 to 80 wt. %, and
- a transition metal component selected from copper and iron components having the oxidation state +2 or +3, in particular the chloride or acetate salts thereof in an amount from 0.1 to 15 wt. %, or
- an ascorbic acid component selected from ascorbic acid, sodium ascorbate, potassium ascorbate, ammonium ascorbate, calcium ascorbate or mixtures thereof in an amount from 5 to 50 wt. %,
- an oxidizing agent component selected from dibenzoyl peroxide, tert.Butylperoxy-3,5,5-trimethylhexanoate, dilauroyl peroxide, tetramethylbutyl hydroperoxide, 2,2-di-(tert-butylperoxy)butane and 2,5-dimethyl-2,5-di-(tert-butylperoxy)hexane or mixtures thereof in an amount from 30 to 80 wt. %, and
- a copper component selected from copper 2-ethylhexanoate, copper naphthenate, copper bis(1-phenylpentan-1,3-dione) complex, copper salicylate or mixtures thereof in an amount from 0.1 to 15 wt. %, wt. % with respect to the amount of the redox initiator system and the copper component, wherein the redox initiator system is optionally dissolved or dispersed in or coated with a film forming component and wherein the components are as described in the present text.

The application device containing the redox initiator system described in the present text can be produced e.g. as follows by applying either of the following methods:

Method A:
a. applying the hydrophobic reducing agent (e.g. ascorbic acid component) as described in the present text together with a solvent to the surface of the application part of the application device,
b. evaporating the solvent,
c. applying the hydrophilic oxidizing agent (e.g. peroxide component) and the hydrophilic transition metal component (e.g. copper component) as described in the present text together with a hydrophilic solvent to the surface of the application part of the application device,
d. evaporating the solvent,
e. optionally applying a film forming component after step (a) or step (d) or after step (a) and (d), or together with step (a) or step (c),
f. optionally conducting a drying step,
wherein the steps are applied in the order (a), (b), (c), (d) or (c), (d), (a), (b).

Method B:
i. applying the hydrophilic reducing agent (e.g. ascorbic acid component) as described in the present text together with a solvent to the surface of the application part of the application device,
ii. evaporating the solvent,
iii. applying the hydrophobic oxidizing agent (e.g. peroxide component) and the hydrophilic transition metal component (e.g. copper component) as described in the present text together with a solvent to the surface of the application part of the application device,
iv. evaporating the solvent,
v. optionally applying a film forming component after step (ii) or step (iv) or after step (ii) and (iv), or together with step (i) or step (iii)
vi. optionally conducting a drying step,
wherein the steps are applied in the order (i), (ii), (iii), (iv) or (iii), (iv), (i), (ii).

For the application of the hydrophilic components typically a hydrophilic solvent is used.

Hydrophilic solvents typically have a log P value $<=1$.

Hydrophilic solvent(s) which can be used include water, methanol, ethanol, propanol, isopropanol, ethyl acetate, acetone and mixtures thereof.

For the application of the hydrophobic components typically a hydrophobic solvent is used.

Hydrophobic solvents typically have a log P value $>=2$ or 3.

Hydrophobic solvent(s) which can be used include hexane, cyclohexane, benzene, toluene, and mixtures thereof.

The nature of the solvent, whether classified as hydrophobic or hydrophilic, is not important.

However, for producing the application device it is advantageous, if the solvent used for applying the second part of the redox initiator system (e.g. hydrophilic oxidizing agent) does not dissolve the components of the previously applied first part of the redox initiator system (e.g. hydrophobic reducing agent) and vice versa.

Film forming components which can be used include those described in the present text above.

The application of the components onto the surface can be accomplished by different means. Useful means include coating, spraying, dipping, printing, freeze-drying. These methods typically require the presence of a solvent.

Drying is typically accomplished by letting the volatile components evaporate. Evaporation can be facilitated e.g. by applying a stream of air and/or heat and/or vacuum, e.g. by using a fan.

If a film forming component is present, the obtained film typically contains the components of the redox initiator system homogeneously dispersed or dissolved in the film produced by the film forming component. The obtained film does typically not contain a solvent anymore.

The thickness of the film is typically within a range from about 0.5 µm to about 100 µm or from about 10 µm to about 50 µm. The thinner the film is, the easier the components of the redox initiator system can dissolve when being combined with the components to be cured.

The redox initiator system described in the present text is located on the surface of an application device. The shape and size of the application device is not particularly limited.

Useful application devices include brushes, sponges, spatulas and dental instruments such as burnishers or condensers.

Specific examples of application devices which can be used are shown in WO 2007/121160 (Kappler et al.), WO 2004/032785 (Dragan), especially the embodiment shown in FIGS. 1 to 5 and the respective description of the FIGS.

The application device may also be a part of or have the shape of a packaging device.

Suitable packaging devices include blister package(s), foil pouch(es), capsule(s), syringe(s), dispensing tip(s) or needle(s), static and dynamic mixer(s).

If the application device forms a part of a packaging device, the application part of the application device may have the shape of a mixing well, a moulding or mixing pad.

Examples of such packaging devices are shown in U.S. Pat. No. 7,097,075 (Peuker et al.), WO 2004/032785 (Dragan) and U.S. Pat. No. 6,105,761 (Peuker et al.).

So-called single use packages were found to be particularly useful.

The application device comprises a handle part and an application part.

The handle part of the application device is the part intended to be held by the practitioner during use. The handle part is not coated with the redox initiator system.

The handle part may be part of a packaging device.

The application part of the application device is the part on which the redox initiator system is located.

The application part may be part of a packaging device.

The application part of the application device may have the shape of a brush, sponge, spatula, mixing pad, mixing well or combination thereof.

The invention is also directed to a kit of parts comprising the application device as described in the present text and a curable composition comprising curable components.

The kit described in the present text is not only suitable to be used in the dental and/or orthodontic area, but to be used in these areas or for use in these areas.

These kinds of products are typically provided to the practitioner with an instruction for use. So, the kit typically also comprise an instruction for use. Possible process steps are described later in the description.

The curable composition comprising curable components can be part of a dental or orthodontic primer or adhesive composition, a dental or orthodontic cement composition, a dental or orthodontic sealant, a dental or orthodontic varnish or dental or orthodontic cavity liner composition or a combination thereof.

Dental adhesives which can be used include e.g. those described in US 2011/224326 A1 (Thalacker et al.) or U.S. Pat. No. 7,700,668 B2 (Thalacker et al.). Dental adhesives are also commercially available e.g. under the name Scotchbond™ Universal (3M Oral Care; 3M ESPE).

Dental cements which can be used include e.g. those described in U.S. Pat. No. 6,982,288 (Mitra et al.) or U.S. Pat. No. 6,939,900 (Ario et al.). Dental cements are commercially available e.g. under the name RelyX™ Unicem (3M Oral Care; 3M ESPE).

Orthodontic adhesives which can be used include e.g. those described in U.S. Pat. No. 6,960,079 (Brennan et al.) or U.S. Pat. No. 6,528,555 (Nikutowski et al.). Orthodontic adhesives are commercially available e.g. under the name Transbond™ (3M Oral Care; 3M Unitek).

The curable components of the curable composition can typically be characterized by one or more of the following features:
Molecular weight (Mw): from 70 to 700 g/mol or from 100 to 600 or from 200 to 500 g/mol;
Viscosity: from 0.1 to 10 Pa*s, or from 0.2 to 5 Pa*s or from 0.5 to 2 Pa*s measured at 23° C.;
Refractive index: from 1.42 to 1.55 (nD);
pH value if brought in contact with wet pH sensitive paper: from 1 to 7.

The ratio with respect to weight of redox initiator system contained on the application device to the composition comprising curable components is typically from 0.1 to 100 up to 15 to 100 or from 0.5 to 100 up to 5 to 100.

Curable components which can be cured by using the redox initiator system described in the present text are typically (meth)acrylates, i.e. components with a one or more (meth)acrylate moieties.

The curable components may also contain an acidic moiety. Thus, the curable components can also be characterized as ethylenically unsaturated acidic compound.

Examples of the acidic moiety include carboxylic acid residues, phosphoric acid residues, or sulfonic acid residues.

In one embodiment, the curable component having an acid group in the molecule can be represented by the following formula

with A being an ethylenically unsaturated group, such as a (meth)acryl moiety,

B being a spacer group, such as (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, and C being an acidic group, with m, n=1, 2, 3, 4, 5 or 6, wherein the acidic group comprises one or more carboxylic acid residues, such as —COOH or —CO—O—CO—, phosphoric acid residues, such as —O—P(O)(OH)OH, or sulphonic acid residues, such as —SO₃H.

Specific examples of ethylenically unsaturated acidic compounds include, but are not limited to glycerol phosphate mono(meth)acrylates, glycerol phosphate di(meth)acrylates, hydroxyethyl (meth)acrylate phosphates, bis ((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl)

phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like. Also monomers, oligomers, and polymers of unsaturated carboxylic acids such as (meth)acrylic acids, aromatic (meth) acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include e.g. 2-(meth)acryloyloxyethyl dihydrogenphosphate, bis[2-(meth)acryloyloxyethyl] hydrogenphosphate, 2-(meth)acryloyloxyethylphenyl hydrogenphosphate, 6-(meth)acryloyl oxyhexyl dihydrogenphosphate, 6-(meth)acryloyloxyhexylphenyl hydrogenphosphate, 10-(meth)acryloyloxydecyl dihydro-genphosphate, bis[10-(meth)acryloyloxydecyl] hydrogenphosphate, 1,3-di(meth)-acryloyloxypropane-2-dihydrogenphosphate, 1,3-di(meth)-acryloyloxypropane-2-phenyl hydrogenphosphate, and bis[5-{2-(meth)acryloyloxyethoxycarbonyl}heptyl] hydrogenphosphate.

The curable components are typically part of a curable composition, which may contain besides the curable components (with and without acidic moieties) filler(s), solvent(s), photoinitiator(s), sensitizer(s) and further additive(s).

The application device with the redox initiator system is typically used for initiating a curing reaction of curable components.

The application device described in the present text is typically used as follows: The redox initiator system located on the application part of the application device is brought in contact with curable components.

Bringing in contact includes dipping or stirring the application part of the application device into or with the composition comprising curable components.

Alternatively, the curable composition comprising the curable components is applied on the surface of the application part of the application device, which may have the shape of a packaging device, being coated partially with the redox initiator system described in the present text.

When doing so, the components located on the surface of the application device will start to dissolve in the composition comprising the curable components.

As a result a composition will be obtained comprising curable components and a redox initiator system. This composition will start to cure.

A typical curing time is from 1 to 10 min or from 1 to 5 min within a temperature range from 20 to 40° C.

The composition obtained by mixing or combining the components of the redox initiator system located on the surface of the application device and the curable components described in the present text is particularly well adapted for use in a wide variety of applications including dental and orthodontic materials, which may be filled or unfilled.

Such materials include direct aesthetic restorative materials (e.g., anterior and posterior restoratives), prostheses, adhesives and primers for oral hard tissues, sealants, cavity liners, orthodontic bracket adhesives for use with any type of bracket (such as metal, plastic and ceramic), crown and bridge cements and the like. These materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

When the material is applied to a tooth, the tooth can optionally be pre-treated with a primer such as dentin or enamel adhesive by methods known to those skilled in the art.

The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Shear Bond Strength (SBS) with Use of a Resin Cement

Bovine teeth were ground flat to expose dentin, polished (grit 320 sandpaper) and rinsed with water. Dedicated adhesive systems of the respective cements were applied according to the manufacturers' instructions. In case of the inventive examples, a coated microbrush was prepared as described under the examples and used to apply Scotchbond™ Universal Adhesive (3M Oral Care; 3M ESPE). In all cases the adhesive was not light-cured. Stainless steel rods (diameter: 4 mm, height: 2 mm) were cemented under pressure (20 g/mm$^2$) onto the teeth at 1 min after start of mixing the cement. Excess was removed using a probe. In the case of RelyX™ Ultimate (3M Oral Care; 3M ESPE), remaining cement was covered with glycerin gel according to the manufacturers' instructions.

2 min after start of mixing the cement, prepared specimens were stored for 10 min at 36° C. Subsequently loading weight and glycerin gel were removed. Specimens were stored for 24 h at 36° C./100% relative humidity. SBS was measured after 24 h (n=5) using a universal testing machine (Zwick Z010, crosshead speed: 0.75 mm/min).

Shear Bond Strength (SBS) without Use of a Resin Cement

Bovine teeth were ground flat to expose dentin, polished (grit 320 sandpaper) and rinsed with water. Scotchbond™ Universal Adhesive (3M Oral Care; 3M ESPE) was applied with the coated brush and rubbed in for 20 s, followed by air drying. The adhesive was not light cured. Stainless steel rods (diameter: 4 mm, height: 2 mm) were placed onto the adhesive. Excess adhesive around the steel rods was removed using a probe. Remaining adhesive was covered with glycerin gel according to the manufacturers' instructions.

SBS was measured after storing the specimens for 24 h at 36° C./100% relative humidity (n=5) using a universal testing machine (Zwick Z010, crosshead speed: 0.75 mm/min).

Viscosity (η)

If desired, the viscosity can be measured with a Haake RotoVisco RV1 device (rotor C60/1 for viscosities up to 8000 mPas or rotor C20/1 for viscosities above 8000 mPas together with stator P61). The viscosity is typically measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94) for the viscosity measurement. Then the rotor is lifted and the material to be measured is given onto the stator (1.0 ml with rotor C60/1 or 0.04 ml with rotor C20/1). Without undue delay, the rotor is lowered into the preliminary adjusted measuring position. The material to be measured is tempered at 23.0° C. The shear rate for the measurement has to be adjusted to a value that the torque is at least 5000 μNm (therefore normally shear rates of 100, 200, 500, or 1000 $s^{-1}$ are used depending on the viscosity of the material to be measured). The measurement is started and run for 60 s. The viscosity values (Pas) are recorded starting 20 s after the start of measurement and the mean value of the recorded values is given as viscosity.

Materials

| Component | Description | Log P/D value* |
| --- | --- | --- |
| Ascorbyl palmitate | Reducing Agent | Log D: 5.01 |
| Di(ascorbyl palmitate) calcium salt | Reducing Agent | Log D: 5.01 |
| Ascorbic acid | Reducing Agent | Log D: −1.92 |
| Copper(II) acetate monohydrate | Transition Metal | Log D: −0.23 |
| Iron II chloride | Transition Metal | Log P: −0.77 |
| Iron III chloride | Transition Metal | Log P: −0.77 |
| Copper(II) di(2-ethylhexanoate) | Transition Metal | Log D: 2.80 |
| Sodium persulfate | Oxidizing Agent | Log D: −5.56 |
| Sodium perborate monohydrate | Oxidizing Agent | Log D: −6.06 |
| Dilauroyl peroxide | Oxidizing Agent | Log P: 9.24 |
| Tetramethylbutyl hydroperoxide | Oxidizing Agent | Lop P: 2.54 |
| Ethanol | Solvent | Log P: −0.16 |
| Water | Solvent | Log P: −0.65 |
| Hexane | Solvent | Log P: 3.13 |
| Iso-propanol | Solvent | Log P: 0.25 |
| Scotchbond ™ Universal (3M Oral Care; 3M ESPE); Lot #605393 | Dental Adhesive | |
| RelyX ™ Ultimate (3M Oral Care; 3M ESPE); Lot #617914 | Dental Resin Cement | |
| Panavia ™ F2.0 (Kuraray); Paste A: Lot #1B0123; Paste B: Lot #160027 | Dental Resin Cement | |
| ED Primer II Liquid A; Lot #1E0028; ED Primer II B (Kuraray); Lot #1C0027 | Dental Primer | |

*calculated based on the respective chemical formula as described in V. N. Viswanadhan, A. K. Ghose, G. R. Revankar, R. K. Robins, "Atomic Physicochemical Parameters for Three Dimensional Structure Directed Quantitative Structure-Activity Relationships", J. Chem. Inf. Comput. Sci. 1989, Vol. 29, 163-172, using the website "www.chemicalize.org", provided by ChemAxon Kft, Budapest, Hungary. Log P/D values are given for pH 2.7

Examples of Hydrophilic Peroxides with Hydrophobic Ascorbic Acid Derivatives

Example 1

0.256 g ascorbyl palmitate was dissolved in 9.744 g ethanol. The head of a microbrush (size M; Microbrush International, Grafton, Wis., USA) was dipped into this solution and dried for 18 h at 23° C.

A second solution was prepared from 9.538 g water, 0.017 g copper(II) acetate monohydrate and 0.445 g sodium persulfate. The head of the same microbrush was dipped into this second solution and dried again for 20 h at 23° C. A picture of such a microbrush is shown in FIG. 1.

Shear bond strength of a stainless steel cylinder luted to dentin with RelyX™ Ultimate was measured according to the method described above.

Example 2

0.259 g di(ascorbyl palmitate) calcium salt was finely dispersed in 9.742 g ethanol. The head of a microbrush (size M) was dipped into this dispersion and dried for 18 h at 23° C.

A second solution was prepared from 9.751 g water, 0.021 g copper(II) acetate monohydrate and 0.232 g sodium persulfate. The head of the same microbrush was dipped into this second solution and dried again for 20 h at 23° C.

Shear bond strength of a stainless steel cylinder luted to dentin with RelyX™ Ultimate was measured according to the method described above.

Example 3

0.130 g ascorbyl palmitate was dissolved in 9.875 g ethanol. The head of a microbrush (size M) was dipped into this solution and dried for 18 h at 23° C.

A second solution was prepared from 9.880 g water, 0.022 g copper(II) acetate monohydrate and 0.114 g sodium perborate monohydrate. The head of the same microbrush was dipped into this second solution and dried again for 20 h at 23° C.

Shear bond strength of a stainless steel cylinder luted to dentin with RelyX™ Ultimate was measured according to the method described above.

Example 4

0.259 g di(ascorbyl palmitate) calcium salt was finely dispersed in 9.742 g ethanol. The head of a microbrush (size M) was dipped into this dispersion and dried for 18 h at 23° C.

A second solution was prepared from 9.880 g water, 0.022 g copper(II) acetate monohydrate and 0.114 g sodium perborate monohydrate. The head of the same microbrush was dipped into this second solution and dried again for 20 h at 23° C.

Shear bond strength of a stainless steel cylinder luted to dentin with RelyX™ Ultimate was measured according to the method described above.

Example 5

0.130 g ascorbyl palmitate were dissolved in 9.875 g ethanol. The head of a microbrush (size M) was dipped into this solution and dried for 1 h at 23° C.

A second solution was prepared from 9.765 g water, 0.040 g iron(III)chloride and 0.231 g sodium persulfate. The head of the same microbrush was dipped into this second solution and dried again for 18 h at 23° C.

Shear bond strength of a stainless steel cylinder luted to dentin with RelyX™ Ultimate was measured according to the method described above.

Example 6

Luting a Stainless Steel Cylinder to Dentin with Scotchbond™ Universal (3M Oral Care; 3M ESPE) Using a Redox Initator Impregnated Brush (without Use of a Cement)

0.513 g ascorbyl palmitate were dissolved in 19.457 g ethanol. The head of a microbrush (size M) was dipped into this solution and dried for 1 h at 23° C.

A second solution was prepared from 9.553 g water, 0.017 g copper (II) acetate and 0.446 g sodium persulfate. The head of the same microbrush was dipped into this second solution and dried again for 18 h at 23° C.

Shear bond strength to dentin was measured according to the method described above.

Example 7

Luting a Stainless Steel Cylinder to Dentin with Panavia™ F2.0 (Kuraray) Using an Impregnated Brush 0.256 g ascorbyl palmitate were dissolved in 9.512 g ethanol. The head of a microbrush (size M) was dipped into this solution and dried for 1 h at 23° C.

A second solution was prepared from 9.557 g water, 0.018 g copper (II) acetate and 0.447 g sodium persulfate. The head of the same microbrush was dipped into this second solution and dried again for 18 h at 23° C.

Shear bond strength of a stainless steel cylinder luted to dentin with Panavia™ F2.0 (Kuraray) according to the manufacturer's instructions was measured according to the method described above, using the brush prepared as described in this example for mixing and applying the appropriate adhesive system consisting of ED Primer II Liquid A and ED Primer II Liquid B.

Examples of Hydrophobic Peroxides with Hydrophilic Ascorbic Acid Derivatives

Example 8

0.261 g ascorbic acid were dissolved in 9.769 g water. The head of a microbrush (size M) was dipped into this solution and dried for 18 h at 23° C.

A second solution was prepared from 4.790 g hexane, 4.769 g isopropanol, 0.036 g iron(II)chloride and 0.438 g dilauroyl peroxide. The head of the same microbrush was dipped into this second solution and dried again for 1 h at 23° C.

Shear bond strength of a stainless steel cylinder luted to dentin with RelyX™ Ultimate was measured according to the method described above.

Example 9

0.256 g ascorbic acid was dissolved in 9.744 g water. The head of a microbrush (size M) was dipped into this solution and dried for 18 h at 23° C.

A second solution was prepared from 9.538 g hexane, 0.017 g copper(II) di(2-ethylhexanoate) and 0.446 g dilauroyl peroxide. The head of the same microbrush was dipped into this second solution and dried again for 1 h at 23° C.

Shear bond strength of a stainless steel cylinder luted to dentin with RelyX™ Ultimate was measured according to the method described above.

Example 10

0.130 g ascorbyl palmitate was dissolved in 9.875 g ethanol. The head of a microbrush (size M) was dipped into this solution and dried for 18 h at 23° C.

A second solution was prepared from 9.554 g hexane, and 0.446 g dilauroyl peroxide. The head of the same microbrush was dipped into this second solution and dried again for 1 h at 23° C.

A third solution was prepared from 9.985 g of a 2:1 water:ethanol mixture and 0.020 g copper(II) acetate monohydrate. The head of the same microbrush was dipped into this third solution and dried again for 20 h at 23° C.

Shear bond strength of a stainless steel cylinder luted to dentin with RelyX™ Ultimate was measured according to the method described above.

Example 11

0.261 g ascorbic acid was dissolved in 9.769 g water. The head of a microbrush (size M) was dipped into this solution and dried for 18 h at 23° C.

A second solution was prepared from 9.843 g hexane, 0.017 g copper(II) di(2-ethylhexanoate) and 0.168 g tetramethylbutyl hydroperoxide (TMBHP). The head of the same microbrush was dipped into this second solution and dried again for 1 h at 23° C.

Shear bond strength of a stainless steel cylinder luted to dentin with RelyX™ Ultimate was measured according to the method described above.

Example 12

0.261 g ascorbic acid was dissolved in 9.769 g water. The head of a microbrush (size M) was dipped into this solution and dried for 18 h at 23° C.

A second solution was prepared from 9.785 g hexane, 0.017 g copper(II) di(2-ethylhexanoate) and 0.253 g tert.-butyl-peroxy-3,5,5,-trimethyl-2-ethylhexanoate (TBPIN). The head of the same microbrush was dipped into this second solution and dried again for 1 h at 23° C.

Shear bond strength of a stainless steel cylinder luted to dentin with RelyX™ Ultimate was measured according to the method described above.

Comparative Example 1

Luting a Stainless Steel Cylinder to Dentin with Scotchbond™ Universal and RelyX™ Ultimate Stainless steel cylinders were luted to dentin using Scotchbond™ Universal (in self-etch application) and RelyX™ Ultimate per manufacturer's instructions. Shear bond strength was measured according to the method described above.

Comparative Example 2

Luting a Stainless Steel Cylinder to Dentin with Panavia™ F2.0 (Kuraray)

Stainless steel cylinders were luted to dentin using the appropriate adhesive system consisting of ED Primer A and ED Primer B, and Panavia™ F2.0 per manufacturer's instructions. Shear bond strength was measured according to the method described above.

The table summarizes the shear bond strength (SBS) and standard deviation (SD) obtained.

|  | dentin SBS [MPa] | SD [MPa] | Log P/D Difference |
|---|---|---|---|
| Example 1 | 25.7 | 11.4 | 10.57 |
| Example 2 | 23.5 | 12.2 | 10.57 |
| Example 3 | 28.0 | 14.8 | 11.07 |
| Example 4 | 41.7 | 4.4 | 11.07 |
| Example 5 | 36.1 | 7.8 | 10.57 |
| Example 6 | 23.2 | 5.9 | 10.57 |
| Example 7 | 31.5 | 5.1 | 10.57 |
| Example 8 | 28.2 | 9.1 | 11.16 |
| Example 9 | 26.3 | 8.3 | 11.16 |
| Example 10 | 39.6 | 8.3 | 4.23 |
| Example 11 | 32.7 | 13.1 | 4.46 |
| Example 12 | 20.3 | 10.0 | 5.96 |
| Comparative Example 1 | 14.4 | 3.4 |  |
| Comparative Example 2 | 13.2 | 10.1 |  |

EVALUATION

If the application device described in the present text was used for applying a dental adhesive to a dental surface, the adhesive strength of an article fixed to the dental surface later could be improved.

What is claimed is:

1. A method for producing an application device, comprising a handle part and an application part, the application part having a surface onto which a redox initiator system is located, the redox initiator system comprising
    a hydrophobic ascorbic acid component as hydrophobic reducing agent,
    a hydrophilic peroxide component as hydrophilic oxidizing agent, and
    a hydrophilic transition metal component,
    the method comprising:
    (a) applying the hydrophobic ascorbic acid component reducing agent together with a solvent to the surface of the application part of the application device,
    (b) evaporating the solvent,
    (c) applying the hydrophilic peroxide component oxidizing agent and the hydrophilic transition metal component together with a solvent to the surface of the application part of the application device,
    (d) evaporating the solvent,
    wherein the steps are applied in the order (a), (b), (c), (d) or (c), (d), (a), (b).
2. The method of claim 1, wherein the
    log P or log D values of the hydrophilic oxidizing agent and hydrophobic reducing agent
    differ from each other by a number of at least 2 calculated for a pH of 2.7, wherein P is the octanol-water partition coefficient for neutral components and D is the octanol-water distribution coefficient for components having ionisable groups.
3. The method of claim 1, the application part further comprising a film forming component.
4. The method of claim 1, wherein the hydrophilic transition metal component is a hydrophilic copper component selected from copper II acetate, copper II chloride, copper II bromide and mixtures thereof.
5. The method of claim 4, the components being present in the following amounts with respect to mol:
    hydrophobic ascorbic acid component: from $1 \cdot 10^{-7}$ to $5 \cdot 10^{-6}$;
    hydrophilic peroxide component: from $5 \cdot 10^{-7}$ to $1 \cdot 10^{-5}$;
    hydrophilic copper component: from $1 \cdot 10^{-8}$ to $1 \cdot 10^{-6}$.
6. A method for producing an application device, comprising a handle part and an application part, the application part having a surface onto which a redox initiator system is located, the redox initiator system comprising
    a hydrophilic ascorbic acid component as hydrophilic reducing agent,
    a hydrophobic peroxide component as hydrophobic oxidizing agent, and
    a hydrophobic transition metal component;
    the method comprising:
    (i) applying the hydrophilic ascorbic acid reducing agent together with a solvent to the surface of the application part of the application device,
    (ii) evaporating the solvent,
    (iii) applying the hydrophobic peroxide oxidizing component and the hydrophobic transition metal component together with a solvent to the surface of the application part of the application device,
    (iv) evaporating the solvent,
    wherein the steps are applied in the order (i), (ii), (iii), (iv) or (iii), (iv), (i), (ii).
7. The method of claim 6, wherein the
    log P or log D values of the hydrophobic oxidizing agent and hydrophilic reducing agent differ from each other by a number of at least 2 calculated for a pH of 2.7, wherein P is the octanol-water partition coefficient for neutral components and D is the octanol-water distribution coefficient for components having ionisable groups.
8. The method of claim 6, the application part further comprising a film forming component.
9. The method of claim 6, wherein the hydrophobic transition metal component is a hydrophobic copper component selected from copper 2-ethylhexanoate, copper naphthenate, copper bis(1-phenylpentan-1,3-dione) complex, copper salicylate and mixtures thereof.
10. The method of claim 9, the components being present in the following amounts with respect to mol:
    hydrophilic ascorbic acid component: from $1 \cdot 10^{-7}$ to $5 \cdot 10^{-6}$;
    hydrophobic peroxide component: from $5 \cdot 10^{-7}$ to $1 \cdot 10^{-5}$;
    hydrophobic copper component: from $1 \cdot 10^{-8}$ to $1 \cdot 10^{-6}$.

* * * * *